United States Patent [19]

Yasuda et al.

[11] Patent Number: 4,657,739

[45] Date of Patent: Apr. 14, 1987

[54] INTEGRAL ELEMENT FOR BIOLOGICAL REACTION AND PROCESS FOR THE PREPARATION THEREOF

[75] Inventors: Yukio Yasuda; Nobuhito Masuda, both of Asaka, Japan

[73] Assignee: Fuji Photo Film Co., Ltd., Kanagawa, Japan

[21] Appl. No.: 590,729

[22] Filed: Mar. 19, 1984

[30] Foreign Application Priority Data

Mar. 17, 1983 [JP] Japan ............................ 58-45060

[51] Int. Cl.$^4$ .................. C12Q 1/00; G01N 33/52; G01N 33/543; G01N 33/548
[52] U.S. Cl. ................................ 422/56; 435/4; 435/14; 435/23; 435/25; 435/805; 436/500; 436/501; 436/518; 436/524; 436/810
[58] Field of Search ............... 436/528, 807, 523, 529, 436/530, 535, 170, 531, 810, 169, 527, 501, 518; 435/174, 177, 4, 7, 178, 178, 179, 180, 182, 805; 162/123, 125, 127, 128; 427/2; 422/56, 57

[56] References Cited

U.S. PATENT DOCUMENTS

| | | | |
|---|---|---|---|
| 3,306,811 | 2/1967 | Sylvester | 162/125 |
| 3,431,162 | 3/1969 | Morris | 162/123 |
| 3,992,158 | 11/1976 | Przybylowicz et al. | 435/808 |
| 4,472,498 | 9/1984 | Masuda et al. | 435/7 |

OTHER PUBLICATIONS

Nature Directory of Biologicals: 1983 Buyer's Guide, p. 220.

*Primary Examiner*—Esther M. Kepplinger
*Assistant Examiner*—David A. Saunders
*Attorney, Agent, or Firm*—Toren, McGeady and Goldberg

[57] ABSTRACT

An integral element for biological reaction comprising at least two layers consisting essentially of:
a composite porous biological reaction layer comprising a fibrous material and a particulate material to which an active substance capable of participating in a biochemical reaction is fixed, and
a porous layer of a fibrous material,
in which:
(1) the weight ratio between the particulate material and the fibrous material ranges from 1:20 to 1:0.3 on a dry basis; and
(2) the particulate material is contained in an amount ranging from 1 to 60 g/m$^2$.

5 Claims, No Drawings

INTEGRAL ELEMENT FOR BIOLOGICAL REACTION AND PROCESS FOR THE PREPARATION THEREOF

BACKGROUND OF THE INVENTION

1. Field of the Invention

This invention relates to an element for biological reaction effectively employable for analysis based on dry chemistry, and to a process for the preparation of the same.

2. Description of Prior Arts

A great number of analytical systems for quantitative analysis of biochemically active components in a liquid sample employing the so called dry analytical element in the form of a sheet of layers is heretofore known (U.S. Pat. No. 3,050,373, etc.). These analytical processes generally utilizes an analytical element containing therein one or more components physically or chemically reactive upon contact to a component to be analyzed and contained in a liquid sample, namely, analyte, and comprises steps of: causing reaction between the reactive component(s) and the analyte introduced into the element within the biological reaction layer provided in the analytical element; and measuring the amount of the reaction product or unreacted component by a photometric or fluorometric measurement or by the use of radioisotope, whereby quantitatively determining the amount of analyte.

The analytical process using a dry analytical element (hereinafter, referred to as dry analytical process) has been widely utilized for various purposes, for example, immunoassay based on an antigen-antibody reaction, and analysis of enzyme or substrate based on an enzymatic reaction, between the analytical procedures employing the dry analytical element are relatively simple. However, poor analytical sensitivity is disadvantageous feature of the dry analytical process.

The present inventors have proposed an analytical element having a biological reaction layer in which a particulate solid carrying a biologically active substance fixed thereto is dispersed in a fibrous material: Japanese Patent Application No. 57(1982)-211382 (corresponding U.S. patent application was filed on Dec. 2, 1983, and EP application was filed on Dec. 2, 1983 under P 33 43 695.9). The reaction layer of this element functions to retain a liquid sample in an amount enough to perform the desired reaction. The present invention provides an improvement of the above-identified element particularly in the quantitative accuracy and handling of the element.

As for a biological reaction layer employing a fibrous material per se is disclosed in Japanese Patent Provisional Publication No. 57(1982)-196153, in which a biologically active substance such as enzyme is directly fixed to the fibers. However, such reaction layer shows difficulty in controlling the amount of an active substance to be fixed to the fibers.

SUMMARY OF THE INVENTION

An object of the present invention is to provide an integral element for biological reaction having an appropriate liquid-holding (or liquid-retaining) capacity and being easily handled.

Another object of the invention is to provide a process for the preparation of the above-identified integral element for biological reaction.

There is provided by the present invention an integral element for biological reaction (optionally referred to as "reaction element" or simply "element") comprising at least two layers consisting essentially of: a composite porous biological reaction layer comprising a fibrous material and a particulate material to which an active substance capable of participating in a biochemical reaction is fixed, and a porous layer of a fibrous material, in which:

(1) the weight ratio between the particulate material and the fibrous material ranges from 1:20 to 1:0.3 on dry basis; and (2) the particulate material is contained in an amount ranging from 1 to 60 g/m$^2$.

The latter porous layer of a fibrous material optionally contain a particulate material such as one described above.

The present invention further provides a process for the preparation of an integral element for biological reaction which comprises:

processing one composition which comprises a particulate material having an active substance capable of participating in a biochemical reaction fixed thereto and a fibrous material and another composition which comprises a fibrous material, both being placed in contact with each other, under such condition that at least one composition is in a slurry state, resulting in formation of an integral structure;

and drying the integrally formed structure.

DETAILED DESCRIPTION OF THE INVENTION

The reaction element of the present invention has, as the basic structure, an integral structure comprising at least two layers combined integrally, namely, a composite porous biological reaction layer comprising a fibrous material and a particulate material to which the above-identified biochemically active substance, and a porous layer of a fibrous material which may contain a particulate material.

The multilayer analytical elements of the conventional arts comprise a plurality of layers prepared by simple processing. Further, although a multilayer analytical element of the integral type is also known, it is formed by coating or pressing by the use of a binder or a similar material, and accordingly the contact between the layers is made through liquid. The term "integral" employed in the present invention means to a layer structure having a specific interface condition between the layers which is different from that of the conventional multilayer analytical element.

In the reaction element of the present invention, there is formed at the interface between the two layers a random structure in which the fibrous materials of the two layers tangle with each other in the three dimensional directions. This three dimensional random structure is formed through not a chemical bonding but a physical force. Nevertheless, such physical binding force between these two layers is sufficiently strong, and no separation can be done between these two layers without breaking the above interface conditions.

One layer constituting the reaction element of the present invention is a composite porous layer comprising a particulate material to which an active substance capable of participating in a biochemical reaction is fixed maintaining an activity thereof in such a manner that the particulate material is dispersed in a matrix of the fibrous material. The particulate material having an active substance fixed thereto is arranged almost uniformly in a space defined by the matrix of the fibrous material.

The other one layer is basically constituted by only a fibrous material, and accordingly, it is termed "simple porous layer" in this specification. The simple porous layer, however, can contain therein a particulate material carrying a certain compound, so as to form a composite porous layer. By preparing the simple porous layer in the form of a composite porous layer, the analytical characteristics of the reaction element is improved and the utility of the element is enlarged.

Accordingly, the present invention further provides an integral element for biological reaction comprising at least two composite porous layers comprising a fibrous material and a particulate material,
in which:

(1) the weight ratio between the particulate material and the fibrous material ranges from 1:20 to 1:0.3 on dry basis;

(2) the particulate material is contained in an amount ranging from 1 to 60 g/m$^2$; and (3) the particulate material of at least one composite porous layer has an active substance capable of participating in a biochemical reaction fixed thereto.

There is no specific limitation on the fibrous material employable in the present invention, so far as the material is substantially inert to a liquid sample and an analyte introduced into the analytical element. Representative examples of the fibrous material include: inorganic fibers such as glass fibers and asbestos; natural organic fibers such as cotton, hemp, pulp and silk; semisynthetic or synthetic fibers such as viscose rayon, cuprammonium rayon, cellulose acetate, partially formalized polyvinyl alcohol, polyethylene, polypropylene, polyvinyl chloride, polystyrene and polyesters (e.g., polyethylene terephthalate). Particularly preferred are glass fibers.

The fibrous material advantageously has thickness in the range of approx. 0.1–5 μm and length in the range of approx. 100–4,000 μm, from a viewpoint of the purpose of the present invention. The fibrous material having such dimensions can be prepared in a conventional manner such as a procedure of processing a mixture of fibers over sieves, for instance, in the range of 10–200 meshes (Tyler Mesh).

The fibrous material can be colored directly with a dye having absorption spectrum in the same region as a spectrum of a measuring light, for instance, a reactive dye or a vat dye, so as to have a light-shielding property.

There is no specific limitation on the particulate material employable in the invention, as far as it is substantially inert to a liquid sample and an analyte introduced into the analytical element. Examples of the particulate material employable in the present invention include non-fibrous materials, for instance, polysaccharide such as agar, agarose, Sepharose TM (beaded agarose available from Pharmacia Fine Chemicals Inc.), Sephadex TM (beaded cross-linked dextran available from Pharmacia Fine Chemicals Inc.) and dextran; polyacrylamide and latex formed by polymerization (or copolymerization) of polymerizable ethylenic monomers; and cellulose powder. Among these materials, non-fibrous materials such as agar, agarose and sepharose are preferably employed because the use of such material can serve to increase the amount of a liquid sample retainable therein per thickness of the biological reaction element, namely, liquid-retaining capacity.

The particulate material preferably is in the form of sticks, in which the ratio of minor axis (thickness or width) to major axis (length) ranges from 1:1 to 1:20. However, there is no specific limitation on shape of the particulate material. For instance, a material of an optional shape such as sphere, circular cone, pyramide, prism or cylinder including its modified or combined shape, can be employed. The mean diameter of the above-mentioned particulate material preferably ranges from 10 to 200 μm.

In the case that the simple porous layer contains a particulate material dispersed therein, the material can be combined with a dye such as one described for dyeing the fibrous material or with a colored pigment (e.g., white powder such as $TiO_2$, $ZnO$ or $BaSO_4$, or white- or metal-lustered powder such as aluminum powder) to have a light-shielding property.

The biologically active substance to be fixed to the particulate material can be any of materials capable of participating in biochemical reactions such as immunological reaction, enzymatic reaction, acceptor-receptor binding reaction, complement binding reaction, and biological aggregation reaction. The biological reaction utilized in the reaction element is automatically determined in view of an analyte under analysis.

The biologically active substance can be dispersed in the simple porous layer in the form that it is fixed to the particulate material, or can be incorporated into an independent auxiliary layer other than the composite porous layer and the simple porous layer. The latter constitution is effectively employed in an analytical system in which the analyte produces a detectable signal via plural reaction stages. Example of this analytical system is a case of analyzing glucose in which hydrogen peroxide is produced in a first composite porous layer containing a glucose oxidase-fixed particulate material and the produced hydrogen peroxide is then introduced into an auxiliary layer such as a second composite porous layer or a simple porous layer capable of providing similar function, to form a color in the presence of peroxidase fixed to the particulate material contained therein.

The integral reaction element having the above-mentioned constitution can be easily prepared in the following manner.

(1)-(i) In the first place, the biologically active substance is fixed to a particulate material. The process for the fixation and other procedures involved in the process such as labeling procedure is described in the aforementioned prior patent applications filed by the present inventors or others, as well as in the texts:

TEXT FOR BIOCHEMICAL EXPERIMENTS, Vol. 1 (Chemistry of Proteins), Vol. 2 (Chemistry of Nucleic Acids), Vol 3 (Chemistry of Fats), and Vol. 4 (Chemistry of Saccharides); compiled by The Society of Biochemistry, Japan, published by Tokyo Kagaku Dozin, Japan, 1977;

ENZYMEIMMUNOASSAY by Kiyoshi Miyai, Rinsho Kensa Vol. 22, No. 11, 1978, extra issue; and METHOD FOR ENZYMEIMMUNOASSAY compiled by Ishikawa, et al., published by Igaku Shoin, Japan, 1978.

The activity of the fixed sustance can be examined in this stage, and the desired activity can be given to the reaction element, if necessary, by adjusting the amount of the particulate material to be employed.

(1)-(ii) A fibrous material is sufficiently loosened, and if necessary a sieving process or the like is applied to the loosened fibrous material to adjust the lengthes of the fibers.

(1)-(iii) The particulate material obtained in the (1)-(i) and the fibrous material obtained in the (1)-(ii) are dispersed in the aforementioned ratio in a dispersing medium (i.e., solvent) such as water or a mixture of water and a water-miscible organic solvent to prepare an aqueous mixture in the form of slurry. In this procedure, a slurry having a desired specific gravity and viscosity can be prepared by employing an appropriately selected medium or by adding a water-soluble material such as sugar to a medium. The selection of the medium or the material to be added can be done by the known density-gradient method.

In the preparation of the slurry, one or more additives employable in an ordinary paper making process such as a dispersant, a viscosity-controller and a antiseptic can be introduced. There is no specific limitation on the method for the preparation of the slurry. For example, any of various methods such as a method utilizing a conventional mixing apparatus, e.g., a magnetic stirrer, stirring blade, homogenizer, or ball mil, and a method utilizing an apparatus employed for a slurry in a conventional paper making process, e.g., a beater.

(2) Independently, a fibrous material is sufficiently loosened and, if necessary, adjusted the length the fibers in the same manner as in the (1)-(ii) above. The so loosed fibrous material is, after introducing thereinto a desired analytical function (e.g., coloration of the fibers to provide thereto a light-shielding property) if necessary, processed to prepare a slurry in the same manner as in the (1)-(iii) above. In the present stage, the above-mentioned analytical function can be alternatively introduced by the use of the aforementioned particulate material. The latter measure is preferable because the coloration can be more effectively done and substances having a variety of functions can be introduced. The determination of the ratio of the particulate material employed, the dispersing procedure, and the adjustment of specific gravity and viscosity of the slurry can be done in the same manner as in the (1)-(iii) above.

(3) One or both of the slurry prepared in (1) and the slurry prepared in (2) are adjusted to give such condition that these slurrys are not mixed therebetween to assure formation on an interface between the phases of these slurrys. The condition that the slurrys are not mixed can be generally accomplished by providing an appropriate difference in the specific gravity between these slurrys. For this purpose, a known density-gradient method can be utilized. Otherwise, the condition that the slurrys are not mixed can be accomplished by providing an appropriate viscosity difference therebetween by adding a water-soluble polymer (i.e., so called viscosity-increasing agent such as synthetic polymer, gum, and polysaccharide) to one or both slurrys.

The above-given statement is concerned with a process involving two wet slurrys. Otherwise, the slurrys can be combined with no adjustment on their physical properties under conditions that one of these slurrys is processed in the form of a layer having a re-wetted matrix. Accordingly, the above-described statement may not be applied to the process in which the layer having re-wetted matrix is involved.

(4) The two slurrys adjusted as above not to give a mixture therebetween are placed in a vessel to make a paper-like material therefrom. In more detail, the slurry of high specific gravity (and/or high viscosity) is arranged to form a lower layer, while the slurry of low specific gravity (and/or low viscosity) is arranged to form a higher layer. Then, these layers are placed on a filter such as a wire-net in a conventional Fourdrinier or cylinder paper making machine, or the like, or milipore filter, and suctioned to remove the dispersing solvent (medium). In the course of this paper-making stage, fibers in these slurrys tangle with each other at the interface between these two slurry phases to form the three-dimensional random structure.

Although the integral element of the present invention can be prepared by the above-mentioned paper making process in which both wet slurrys are simultaneously done to give an integral paper-like material, other processes can be also utilized to prepare the integral material. For instance, the integral material of the invention can be prepared by, in the first place, making a dry paper-like layer from one slurry, and in the second place, placing the dry layer (sheet) on the other slurry layer to make the reaction element. The desired inteface showing the three-dimensionally tangling structure can be produced in that manner. This procedure is advantageously employed in the preparation of the reaction element comprising an integral structure of more than two layers. In summary, the interface showing the three-dimensionally tangling structure can be produced, as far as one of the slurrys are combined with the other slurry layer or re-wetted dry layer under such condition that the former slurry contains the fibrous material dispersed at random therein.

(5) The paper-like material is then defined on the thickness by means of a member or members providing a certain clearance. For instance, the material is pressed between two flat plates to give an integral layer having a certain thickness. Otherwise, the paper-like material can be caused to pass through between rollers giving a slit of a predetermined clearance. Also employable are other methods, detailed of which are described in the aforementioned patent applications filed by the present inventers or the like. The preferred range of the thickness defined as above is from 100 to 2,000 $\mu$m. The material is then dried without substantially varying the so defined thickness.

The dry procedure is preferably carried out at a relatively low temperature. The freeze-drying procedure is particularly advantageous because it facilitates to dry the thickness-defined material under condition that the biologically active substance fixed to the particulate material maintains its activity even after being subjected to the drying procedure.

Otherwise, the drying procedure can be carried out in advance of the stage of defining the thickness of the integral paper-like material.

In the above, the description is a given with respect to an integral reaction element consisting essentially of two layers. However, the integral element of the present invention is not restricted to the two-layer structure. Thus, the integral reaction element of the invention can comprise three or more layers, and the constitution of the reaction element can be determined depending upon properties of the analyte, in view of the mechanism or analytical process involved.

Between the composite porous layer and the simple porous layer of the invention, a net-like sheet can be inserted, provided that the net-like sheet does not disturb the formation of the three-dimensionally tangling structure between the fibers at the interface. The net-like sheet can be a net of nylon (i.e., polyamide) or polyester, a net for collecting plankton, or a veil.

A protective layer made of a fibrous material only can be provided to the reaction element on the composite porous layer side so that drop-out of the particulate material in the paper making stage is effectively prevented.

Although the biological reaction layer can be utilized as such, it is preferably employed in the form of a multilayer analytical element in which plural layers are laminated, so as to enhance the analytical accuracy. The constitution of the multilayer analytical element can be selected according to the constitutions described in the aforementioned patent applications or the known arts.

The multilayer analytical element having the reaction element of the present invention can be utilized for the analytical procedure in the following manner.

A certain amount of a liquid sample containing analyte is spotted (dropped, etc.) on a upper reaction element of the multilayer analytical element or an auxiliary layer provided on the upper reaction element (e.g., filter layer, spreading layer, reagent layer, etc.). In the reaction element, a biochemical (biological) reaction relating to the active substance fixed in the element proceeds to produce a signal corresponding to the amount of the analyte. Thus produced signal is then measured in the conventional manner to accomplish the desired quantitative analysis.

The reaction element of the present invention has the following advantageous features.

(1) The element shows high liquid-retaining capacity, and accordingly the analytical accuracy is enhanced and the period for the analytical operation can be shortened.

(2) The element is in such an integral form that the transfer of liquid between the constitutional layers can proceed uniformly.

(3) The element can be formed in such manner that each layer can be produced as an extremely thin layer. Accordingly, the actually effective content of the substance participating in the biochemical reaction relatively increases, as compared with the case of using the conventional element, the comparison being made under condition that the liquid sample is introduced at the same volume. For this reason, the amount of signal produced per a certain period increases, and thus the reaction time can be shortened, as well as the sensitivity is enhanced.

(4) The element is so formed that two or more thin layers are integrally combined to facilitate the handling.

The present invention is further described by the following examples. But, these examples shall be by no means construed to restrict the present invention.

EXAMPLE 1

Preparation of Reaction Element for Determination of Human•IgG (1) Preparation of Anti-human•IgG rabbit•IgG-fixed Agarose In 20 ml. of 0.1M sodium hydrogencarbonate buffer (pH 8.5) containing 0.5M sodium chloride was dissolved 10 mg. of anti-human•IgG rabbit•IgG (available from Miles Laboratories Corp.). The resulting solution was mixed with 100 ml. of a swollen gel of CNBr-activated Sepharose 4B (available from Pharmacia Fine Chemicals Inc.) having been washed with 1 mM aqueous HCl. The mixture was reacted under stirring at 4° C. for 16 hours. After the reaction was complete, the reaction liquid was filtered off over a glass filter. The resulting gel was mixed with 50 ml. of 1M monoethanolamine-hydrochloric acid (pH 8.5), and the reaction was carried out under stirring at 4° C. for 2-3 hours. After the reaction was complete, the resulting gel was washed alternatingly with three portions of 0.1M acetate buffer (pH 4.0) containing 1M sodium chloride and 0.1M borate buffer (pH 8.0) containing 1M sodium chloride in the conventional manner. The gel was washed finally with 0.1M glycine buffer (pH 8.0) containing 0.1% sodium azide and 0.1M sodium chloride. Thus washed gel was then stored in the same buffer solution.

(2) Preparation of Reaction Element for Determination of Human IgG

A glass fiber filter GA-100 (available from Toyo Filter Paper Co., Ltd., Japan) was cut to give a square piece (approx. 2 mm×2 mm) and dispsersed in water to break down the filter structure. Subsequently, the resulting dispersion was processed on sieves of Tyler Standard Mesh No. 32 and No. 16, to collect glass fibers capable of passing through the No. 16 mesh sieve but not passing through the No. 32 mesh sieve.

The solid content of the resulting dispersion was determined by filtering a 10 ml. portion thereof over a microfilter having of pore size 0.45 $\mu$m. (available from Fuji Photo Film Co., Ltd., Japan) and the remaining glass fibers were freeze-dried. After removal of the microfilter, the collected glass fibers were weighed to indicate that the solid content was 7.0 mg.

150 ml. of the above-obtained dispersion (solid content 105 mg.) was mixed under stirring with 250 ml. of 30% aqueous glycerol solution to give a slurry A. Independently, 100 ml. (solid content 70 mg.) of the above-obtained glass fiber dispersion, 100 ml. of water and 3 ml. of the anti-human•IgG rabbit•IgG-fixed Sepharose were weighed and mixed under stirring to give a slurry B.

A microfilter having pore size 0.45 $\mu$m (available from Fuji Photo Film Co., Ltd.) was provided onto a filtering appratus (diameter 142 mm, available from Millipore Corp.), and further the polyacrylic resin-made cylinder was placed thereon. In the so constituted appratus, the slurry A and slurry B were sequentially poured gradually to form two layers having different specific gravity. After confirming the formation of an interface between the two separate layers, the layers were filtered under reduced pressure (pressure difference: 100 mgHg.) to prepare the desired reaction element in a paper-like form.

After the filtering was complete, the collected materials together with the microfilter were frozen on a flat stainless steel-made net, and then freeze-dried. The dried material was pressed between two stainless steel-made flat plate having a clearance of 250 $\mu$m to define the thickness. Thus, the desired reaction element (I) for determination of human•IgG was obtained.

The same procedure as above was repeated except that the anti-human•IgG rabbit•IgG-fixed Sepharose was replaced with the same amount of Sepharose 4B (available from Pharmacia Fine Chemicals Inc.) containing no antibody to prepare a slurry B. Thus, a reaction element (II) was prepared.

Moreover, an element containing anti-human•IgG rabbit•IgG in the same amount dispersed uniformly throughout the element was prepared in the following manner, for comparison with the reaction element (I) of the present invention.

250 ml. (solid content 175 mg.) of the aforementioned glass fiber dispersion was mixed with 3 ml. of the anti-human•IgG rabbit•IgG-fixed Sepharose gel prepared in the (1) above to obtain a slurry. The resulting slurry was filtered on the same filtering apparatus to form a paper-like material, which was then freeze-dried and defined on the thickness to give a reaction element (III).

A slurry consisting of 100 ml. (solid content 70 mg.) of the aforementioned glass fiber dispersion, 100 ml. of water and 3 ml. of the antibody-fixed Sepharose gel was filtered in the same manner to form a paper-like material. The paper-like material was then freeze-dried. The resulting single layer structure was easily broken after removal of the microfilter and was not available as the analytical reaction element because of the handling difficulty.

(3) Evaluation of Reaction Element

Ten circular specimens (diameter 13 mm) were cut out of each of the reaction elements (I), (II), and (III) prepared in the (2) above, and placed on a polytetrafluoroethylene plate. On each of the specimens was dropped 80 μl. of 2% human serum albumin solution (0.1M NaCl-0.1M glycine Na buffer: pH 9.0) containing FITC-labeled human IgG (available from Cappel Laboratories) in an amount of 10 μg/ml. The specimen was kept at 30° C. for 10 min. for carrying out the reaction. Just after lapse of 10 min., each specimen was placed on a microfilter (pore size 0.45 μm, available from Fuji Photo Film Co., Ltd.) provided on the filtering appratus under reduced pressure condition to remove the unreacted FITC human IgG.

Each specimen was then transferred onto a quartz plate (2×3 cm), and received 80 μl. of the above-mentioned glycine buffer solution applied thereto through dropping. The specimen was then subjected to fluorometry. The fluorometry at the exciting wavelength 492 nm and the measuring wavelength 525 nm using a fluorometer (850 type, available from Hitachi Inc., Japan) to have a relative fluorescence strength. Thereafter, a mean value ($\bar{x}$) and a standard deviation ($\sigma$) were obtained through calculation.

The results are set forth in Table 1.

TABLE 1

| | Relative Fluorescence Strength* |
|---|---|
| Reaction Element (I) (according to the invention) | 685 ± 13 |
| Reaction Element (II) (blank sample) | 53 ± 2 |
| Reaction Element (III) (Comparison Example) | 322 ± 11 |

*($\bar{x} \pm \sigma$)

The results set forth in Table 1 clearly indicate that the reaction element (I) of the present invention is superior in the reactivity.

EXAMPLE 2

Reaction Element for Glucose Determination (1) Preparation of Glucose Oxidase-Fixed Sepharose A glucose oxidase-fixed Sepharose gel (GOD-fixed Sepharose gel) was prepared by the same procedure as in Example 1-(1) except that the anti-human•IgG rabbit•IgG solution was replaced with a solution of 100 mg. of glucose oxidase (Sigma Chemicals) in 10 ml. of 0.1M sodium hydrogencarbonate buffer (containing 0.5M sodium chloride, pH 8.5).

(2) Preparation of Reaction Element for Glucose Determination 120 ml. (solid content 120 mg.) of a glass fiber dispersion prepared in the same manner as in Example 1-(2) (solid content 10 mg./10 ml. of dispersion) and 200 mg. of a pearl pigment TP-900 consisting mainly of mica having particle size in the range of approx. 50 to 100 μm. (available from Teikoku Kako Co., Ltd., Japan) were mixed under stirring to prepare a slurry. The resulting slurry was processed on the filtering apparatus described in Example 1-(2) to form a paper-like material. In carrying out this stage, a nylon-made mesh (hexagonal cloth piece having pore size of approx. 1 mm, available from Toray Corp., Japan, which had been cut to a circular piece having diameter 115 mm, being smaller than the inner diameter of the polyacrylic resin-made cylinder, namely 120 mm) was placed on the slurry prior to the paper-making process, whereby the produced paper-like material is reinforced by the nylon-mesh. The paper-like material was then freeze-dried to form an auxiliary layer showing a reflective function.

Independently, 70 ml. of the same glass fiber dispersion (solid content 70 mg.) as described above, 100 ml. of distilled water, and 3 ml. of GOD-fixed Sepharose gel prepared in the (1) above were mixed under stirring to prepare a slurry. The resulting slurry was processed on the microfilter (pore size 0.45 μm.) provided on the filtering apparatus as described above, to form a paper-like material. In carrying out this stage, the above-obtained reflective auxiliary layer is placed on the slurry prior to the paper-making process in such manner that the nylon mesh side faced the slurry. The formed paper-like material was then freeze-dried and pressed by means of a set of stainless steel-made plates having clearance 250 μm to give a reaction element (IV).

For comparison, a reaction element (V) was prepared in the same manner as above except that the GOD-fixed Sepharose gel was replaced with the same amount of Sepharose 4B gel (Pharmacia Fine Chemicals, Inc.)

(3) Analysis using Reaction Element for Glucose Determination (Preparation of Calibration Curve)

1,000 units of peroxidase prepared from horse raddish (available from Sigma Chemicals), 5 g. of orthophenylene diamine (available from Wako Junyaku Co., Ltd., Japan) in the form of a methanol solution (10 ml.), and 0.2 g. of a gelatin hardener were mixed with 100 ml. of 10% aqueous lime-processed gelatin solution. The resulting mixuture was coated on a glow discharge-processed transparent polyethylene terephthalate (PET) support (thickness 180 μm.) and dried to give a reagent layer of 10 μm. thick (dry basis).

The reagent layer formed on the support and the reaction element (IV) or (V) prepared in the (2) above were punched to give circular sheets having diameter of 13 mm. Thus obtained circular sheets were combined in such manner that the gelatin reagent layer was in contact with the auxiliary layer to prepare an analytical element.

Independently, 0.1M phosphate buffers (containing 0.8% sodium chloride) containing glucose in amounts of 0.5, 10, 20, 50, 100 and 500 mm/dl, respectively, were prepared. The phosphate buffers were dropped on each of the analytical elements in an amount of 75 μl. per each, and the reaction was caused at 30° C. Just after lapse of 10 min., the optical density of the color formed on the element was photometrically measured on each analytical element from the transparent PET support side. The measurement was carried out by means of a reflection densitometer (manufactured by Fuji Photo Film Co., Ltd.) using a blue light. The results are set forth in Table 2.

TABLE 2

| | Glucose Content (mg/ml) | | | | | | |
|---|---|---|---|---|---|---|---|
| | 0 | 5 | 10 | 20 | 50 | 100 | 500 |
| Element IV | 0.45 | 0.57 | 0.75 | 1.18 | 1.47 | 1.98 | 2.56 |
| Element V | 0.44 | 0.45 | 0.45 | 0.44 | 0.43 | 0.42 | 0.40 |

It is apparent that the reaction element IV according to the present invention gives a satisfactory calibration curve proportional to the glucose content.

EXAMPLE 3

Preparation of Reaction Element for Determination of Trypsin (1) Preparation of L-Phenylalanyl-L-seryl-L-arginine-4-methylcumaryl-7-amide fixed Sepharose 10 mg. of t-butyloxycarbonyl-L-phenylalanyl-L-seryl-L-arginine-4-methylcumaryl-7-amide (t-BOC-Phe-Ser-Arg-MCA: available from Protein Research Foundation, Oosaka, Japan) was dissolved in 10 ml. of 98% forminc acid. To the solution was added 0.5 ml. of 12N hydrochloric acid. The mixture was caused to react at room temperature for 1 hour, and freeze-dried. The residue was then dissolved in 10 ml. of 0.1M hydrogencarbonate buffer (pH 8.0) containing 0.5M sodium chloride. The solution was mixed with 100 ml. of an activated CH Sepharose 4B (Pharmacia Fine Chemicals Inc.) having been previously swollen and washed, and the resulting mixture was caused to react under stirring at 4° C. for 16 hours. After the reaction was complete, the remaining reactive groups were inactivated in the conventional manner by addition of 1M ethanolamine. Subsequently, the gel was washed with 0.1M glycine buffer (pH 8.0) containing 0.1M sodium chloride and stored in the same buffer solution.

(2) Preparation of Reaction Element for Determination of Trypsin

To 120 ml. (solid content 120 mg.) of a glass fiber dispersion prepared in the same manner as in Example 1-(2) (solid content 10 mg/10 ml of dispersion) was added 200 ml. of 30% aqueous glycerol solution to prepare a slurry C.

To 70 ml. of the same glass fiber dispersion (solid content 70 mg.) was added 100 ml. of distilled water, and to the mixture was further added under stirring 3 ml. of the Phe-Ser-Arg-MCA fixed Sepharose gel prepared in the (1) above. Thus, a slurry D was prepared.

The slurry A, 100 ml. of distilled water and the slurry B were slowly placed in this order in the polyacrylic resin-made cylinder provided on the microfilter in the same manner as in Example 1-(2). The slurry layers were then filtered under reduced pressure (pressure difference: 100 mmHg) to form a paper-like material. The resulting material was freeze-dried to give the desired reaction element (VI) for determination of trypsin.

(3) Analysis using Reaction Element for Determination of Trypsin

The reaction element prepared in the (3) above was cut to give a square specimen (1 cm × 1 cm) and placed on a quartz plate. On the specimen was dropped 100 μl. of 0.1M hydrogencarbonate buffer (pH 8.5) containing trypsin treated with L-1-tosylamido-2-phenylethyl chloromethyl ketone (TPCK; available from Sigma Chemicals) in amounts of 0.5, 10, 20, 50 and 100 μg/ml., repsectively. The element was then warmed to 30° C. to cause reaction. Just after lapse of 10 min., the specimen was subjected to fluorometry at the exciting wavelength 360 nm and the measuring wavelength 440 nm using a fluorometer (850 type, available from Hitachi Inc.) to have a relative fluorescence strength. The results are set forth in Table 3.

TABLE 3

| | TPCK-treated Trypsin Content (mg/ml) | | | | | |
|---|---|---|---|---|---|---|
| | 0 | 5 | 10 | 20 | 50 | 100 |
| Relative Fluorescence Strength | 25 | 40 | 58 | 99 | 220 | 410 |

It is apparent that the reaction element according to the present invention gives a satisfactory calibration curve proportional to the trypsin content.

EXAMPLE 4

Preparation of Reaction Element for Determination of Thyroxine (1) Preparation of Anti-$T_4$ Rabbit•IgG-fixed Sepharose Gel To 120 ml. (solid content 96 mg.) of a glass fiber dispersion prepared in the same manner as in Example 1-(2) (solid content 8 mg/10 ml of dispersion) was added 7 ml of an orange-colored Sepharose 4B gel (Pharmacia Fine Chemicals Inc.) dyed with Mikacion Brill. Orange GS (available from Nippon Kayaku Co., Ltd., Japan). The mixture was then stirred to give a slurry. The resulting slurry was processed in the same manner as in Example 2-(2) to give a colored auxiliary layer accompanied with a nylon mesh.

(2) Preparations of Reaction Element for $T_4$ Determination Accompanied with Layer for Prevention of Dropping of Antibody-fixed Sepharose Particles and Colored Layer To 10 ml. (solid content 8 mg.) of the glass fiber dispersion described in the (2) above was added under stirring 100 ml. of 20% aqueous saccharose solution, to prepare a slurry E.

Independently, 100 ml. of 0.2M glycine Na buffer (pH 9.0) and 2.5 ml. of the $T_4$ antibody-fixed Sepharose gel were added under stirring 90 ml. of the same dispersion (solid content 72 mg.) to prepare a slurry F.

The slurry E and slurry F were slowly placed in this order in the polyacrylic resin-made cylinder provided on the microfilter. After the colored auxiliary layer accompanied with the nylon mesh was slowly placed on the slurry in such manner that the nylon mesh side faced the slurry, and then filtered. The filtrate was then freeze-dried and defined on the thickness under pressure to give the desired analytical element for $T_4$ determination having the dropping-preventive layer, the nylon mesh and the colored auxiliary layer.

The resulting reaction element can be laminated on a transparent support (e.g., PET support) having a binder reagent layer which contains FITC-labeled $T_4$ and employed as an analytical element for $T_4$ determination.

We claim:

1. In an integral element for quantitative analysis of biochemically active components in a liquid sample which comprises a porous reaction layer comprising a fibrous material and an active substance being active to said biochemically active components and a second porous layer superposed on the porous reaction layer, the improvement which comprises:

said porous reaction layer containing a particulate material in an amount ranging from 1 to 60 g/m$^2$, the weight ratio of the particulate material to fibrous material being from 1:20 to 1:0.3 on a dry basis, the active substance being fixed to the particulate material, the porous reaction layer and the second porous layer being superposed under the condition that the fibrous material of the reaction layer and the fibrous material of the second porous layer are tangled with each other on the interface between these layers.

2. The integral element of claim 1 wherein said particulate material is in the form of sticks having a ratio between thickness and length ranging from 1:1 to 1:20.

3. The integral element of claim 1 wherein said particulate material is selected from the group consisting of agar, agarose and beaded agarose.

4. The integral element of claim 1 wherein the fibrous materials of the porous reaction layer and the second layer have a thickness ranging from 0.1 to 5 μm and a length ranging from 100 to 4,000 μm.

5. The integral element of claim 1 wherein the fibrous materials of the porous reaction layer and the second layer are glass fibers.

* * * * *